(12) United States Patent
Cameron et al.

(10) Patent No.: US 6,262,076 B1
(45) Date of Patent: Jul. 17, 2001

(54) PHARMACEUTICAL COMPOSITION FOR USE IN THE TREATMENT OF DIABETIC NEUROPATHY

(75) Inventors: Norman E. Cameron, Aberdeen (GB); Hideaki Kihara; Ryota Yoshimoto, both of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/493,252

(22) Filed: Jan. 28, 2000

(51) Int. Cl.$^7$ .................................................. A61K 31/445
(52) U.S. Cl. ............................................ 514/316; 514/866
(58) Field of Search ...................................... 514/316, 866

(56) References Cited

U.S. PATENT DOCUMENTS 5,932,593 * 8/1999 Makino et al. ...................... 514/316

FOREIGN PATENT DOCUMENTS 8-003135   1/1996   (JP) .

* cited by examiner

Primary Examiner—Frederick Krass
(74) Attorney, Agent, or Firm—Oblon, Spivak, McClelland, Maier & Neustadt, P.C.

(57) ABSTRACT

Disclosed is a pharmaceutical composition for use in the treatment of diabetic neuropathy, which comprises a piperidine derivative represented by the following general formula (1) or a pharmaceutically acceptable salt thereof as an effective ingredient:

(1)

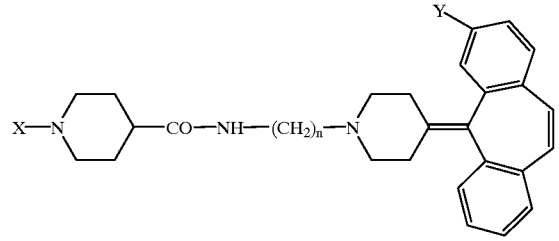

wherein n is an integer of 2 of 3, Y is a hydrogen atom or halogen atom, and X is a formyl group, acetyl group or hydrogen atom.

4 Claims, 2 Drawing Sheets

PHARMACEUTICAL COMPOSITION FOR USE IN THE TREATMENT OF DIABETIC NEUROPATHY

BACKGROUND OF THE INVENTION

The present invention relates to a pharmaceutical composition for use in the treatment of diabetic neuropathy. In particular, the present invention relates to a pharmaceutical composition for use in the treatment of diabetic neuropathy caused by a microvascular circulatory disturbance.

The term "diabetic neuropathy" indicates a neuropathy caused by a chronic hyperglycemic condition. The diabetic neuropathy is roughly classified into groups of multiple neuropathy, autonomic neuropathy and single neuropathy. Diabetic neurosis usually indicates a symmetrical, distal, multiple neuropathy mainly causing sensory disturbance. Both multiple neuropathy and autonomic neuropathy are neuropathies characteristic of diabetics.

A cause for the diabetic neuropathies is a chronic hyperglycemic state. However, the mechanism of the crisis has not been fully elucidated yet. For the crisis mechanism of the neuropathy caused by hyperglycemia, there are two main theories, i.e. vascular dysfunction and disturbed metabolism.

According to the vascular dysfunction theory, the blood flow is disturbed by changes of the blood abnormalities (such as acceleration of platelet aggregation, increase of the blood viscosity and decrease of the red blood-cell deformity) or by changes of the blood vessel abnormalities (such as reduction of the production of nitric oxide from the endothelial cells of blood vessels and acceleration of the reactivity on vasoconstrictive substances), then the hypoxia of nerves is caused, and finally the nerves are degenerated. For example, when the platelet aggregation is accelerated by the chronic hyperglycemic state, the microvascular disturbance is caused to result in diabetic neuropathy.

On the other hand, in the disturbed metabolism theory, the causes thereof can be classified into a group of the activation of the polyol metabolic pathway and the non-enzymatic protein glycosylation, It is commonly accepted that both vascular dysfunction theory and disturbed metabolism theory are correct. Also, it is considered that the disturbed metabolism mainly causes the initial stage of the diabetic neuropathy and, as the disease reaches an advanced stage, the concern of the-vascular dysfunction increases.

Epalrestat [Japanese Patent Unexamined Published Application (hereinafter referred to as "J. P. KOKAI") No. Sho 57-40478; EP 47109A] which is an aldose reductase inhibitor effective in inhibiting the activation of the polyol metabolic pathway is used as a remedy for diabetic neuropathy. However, this remedy is not so effective and is unsatisfactory for curing the human disease, while the symptoms of animals can be almost completely recovered with it. Reasons for this phenomenon are, for example, that the effects of this remedy vary depending on the species and that the amount of the aldose reductase varies among the patients.

Under these circumstances, not only remedies developed on the basis of the disturbed metabolism theory but also remedies developed on the vascular dysfunction theory are being developed. It is known that vasodilators such as α1 receptor antagonists, angiotensin receptor antagonists, angiotensin converting enzyme inhibitors, calcium channel blockers, endothelin receptor antagonists, prostaglandin preparations and nitric oxide donors inhibit the neuropathy of streptozotocin induced diabetic rats or they even improve the neuropathic symptoms. However, most of these vasodilators have a blood pressure-lowering effect which is undesirable for the patients with diabetic neuropathy.

SUMMARY OF THE INVENTION

The object of the present invention is to provide a pharmaceutical composition for use in the treatment of diabetic neuropathy.

After intensive investigations made with diabetes model rats, the inventors have found that specified piperidine derivatives disclosed in J. P. KOKAI No. Hei 8-3135 and known as serotonin antagonists or antithrombocytic agents having an effect of inhibiting the platelet aggregation have an extremely high curative effect on diabetic neuropathy when they are used in such a dose that they do not cause the lowering of the blood pressure. The present invention has been completed on the basis of this finding.

Namely, the present. invention relates to a pharmaceutical composition for use in the treatment of diabetic neuropathy, which comprises a piperidine derivative represented by the following general formula (1) or a salt thereof as an effective ingredient:

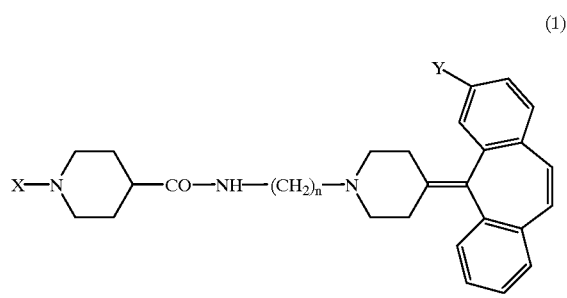

(1)

wherein n is an integer of 2 or 3, Y is a hydrogen atom or halogen atom, and X is a formyl group, acetyl group or hydrogen atom.

There is also provided a method for the treatment of diabetic neuropathy which comprises the step of administering an effective amount of a piperidine derivative represented by the following general formula (1) or a salt thereof to a patient with diabetic neuropathy.

The compounds of the present invention are particularly effective when diabetic neuropathy is caused by a microvascular circulatory disturbance and particularly when the microvascular circulatory disturbance therein is caused by accelerated platelet aggregation. In the compounds of general formula (1) in the present invention, a compound of the formula wherein n is 2, Y is a hydrogen atom and X is a formyl group is particularly effective.

DESCRIPTION OF THE PREFERRED EMBODIMENTS

Figure 1:
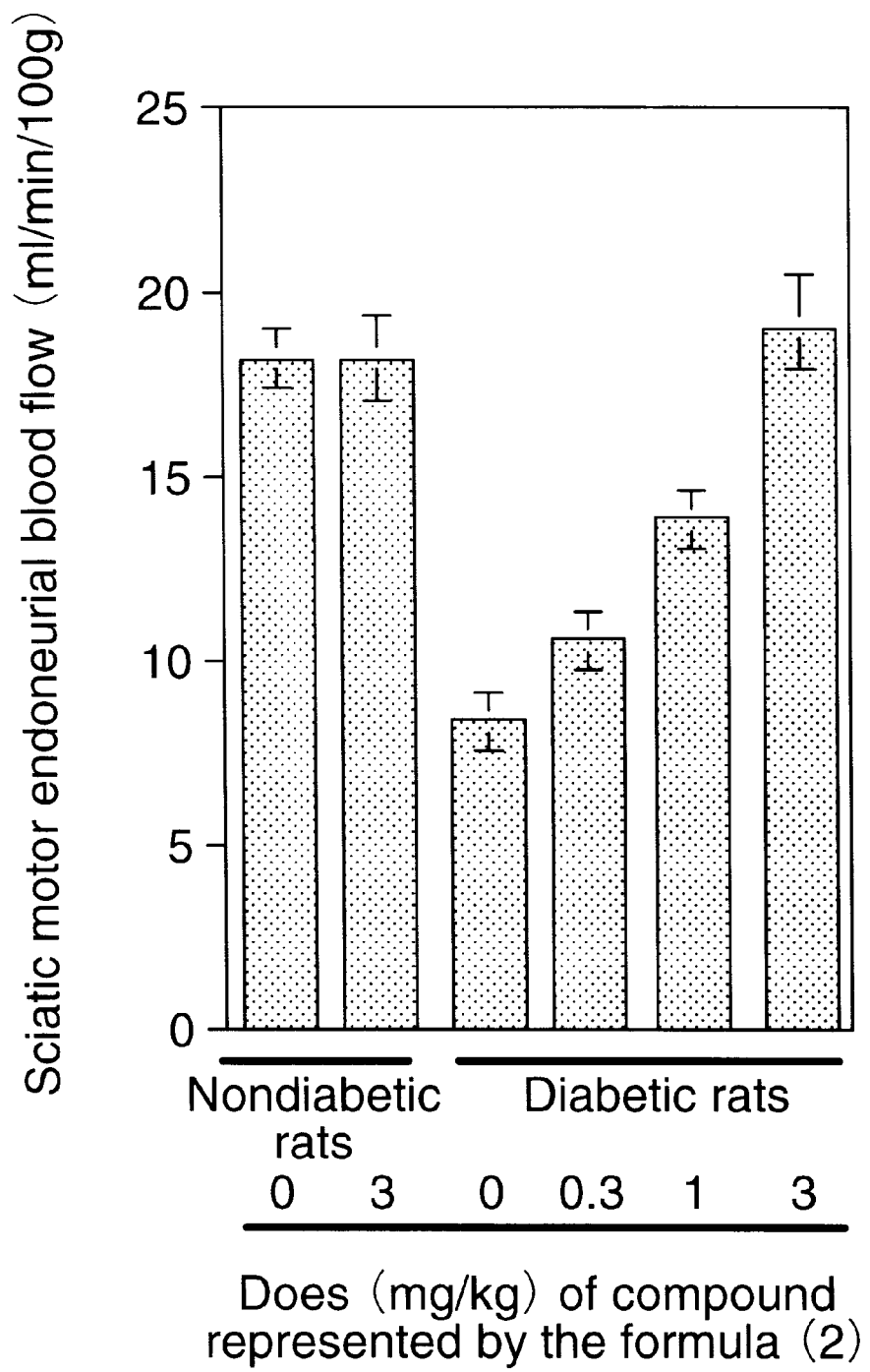
FIG. 1 shows the effects of the compound of formula (2) on the sciatic motor endoneurial blood flow of each of non-diabetic rats and diabetic rats.

Piperidine derivatives represented by general formula (1) and used in the present invention are well-known compounds which can be produced by, for example, a method disclosed in J. P. KOKAI No. Hei 8-3135. To give an example, 1-formyl-N-(2-(4-(5H-dibenzo[a,d]cycloheptene-5-yliden)-1-piperidinyl))ethylisonipecotamide 10 of following formula (2) which is included by general formula (1) is prepared as follows: Di-t-butyl dicarbonate is reacted with 2-aminoethyl bromide hydrobromide in the presence of sodium hyd-rogencarbonate to obtain N-t-butoxycarbonyl-2-bromoethylamine. Then, this compound is condensed with 4-(5H-dibenzo[a,d]cycloheptene-5-yliden)piperidine in the presence of a base such as triethylamine to obtain 4-(5H-dibenzo[a,d]cycloheptene-5-yliden)-1-(2-t-butoxycarbonylamino)ethyl)piperidine. t-Butoxycarbonyl group is removed from the obtained compound with 4 M hydrochloric acid/dioxane or the like. The obtained compound is condensed with 1-formylisonipecotic acid in the presence of a condensing agent such as 1-(3-dimethylaminopropyl)-3-ethylcarbodiimide to obtain the intended compound.

(2)

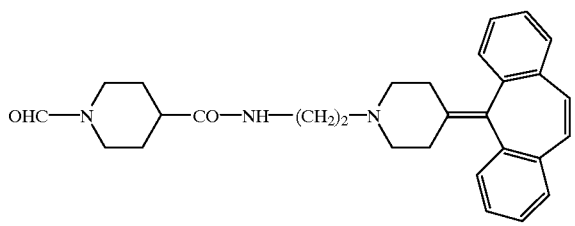

The compound thus obtained is isolated in the form of the free compound or a salt thereof. The isolation can be conducted by the extraction, concentration, distillation, crystallization as described in J. P. KOKAI No. Hei 9-176119, and various chromatographic methods.

The pharmaceutically acceptable salts of the piperidine derivatives used in the present invention include acid addition salts thereof with mineral acids such as hydrochloric acid, hydrobromic acid, sulfuric acid, nitric acid and phosphoric acid, or organic acids such as formic acid, acetic acid, lactic acid, salicylic acid, mandelic acid, citric acid, oxalic acid, maleic acid, fumaric acid, tartaric acid, tannic acid, malic acid, tosylic acid, methanesulfonic acid and benzenesulfonic acid.

When the piperidine derivative or pharmaceutically acceptable salt thereof is used as the remedy for diabetic neuropathy according to the present invention, the dosage forms thereof include tablets, powders, pills, granules, sugar-coated tablets, emulsions, capsules, solutions, injections and suppositories. These pharmaceutical preparations can be produced with a commonly used carrier, filler and other assistants by an ordinary method.

The preparation may be administered either orally or parenterally. The dosage, which varies depending on the age, body weight, and conditions of the patient and also on the administration method, is usually 0.01 to 500 mg/day, preferably 0.1 to 50 mg/day, in the oral administration for adults; and is usually 1 μg g/day to 100 mg/day, preferably 0.01 to 10 mg/day, in the parenteral administration for adults. When the compounds of the present invention are used as the remedies for diabetic neuropathy, a particularly excellent effect thereof can be obtained by the oral administration.

EXAMPLE 1

Streptozotocin (40–45 mg/kg) was put into the abdomen of each of male Sprague-Dawley rats (19 weeks old) to induce diabetes. Six weeks after injection of streptozotocin, a solution of 1-formyl-N-(2-(4-(5H-dibenzo[a,d] cycloheptene-5-ylidene)-1-piperidinyl)) ethylisonipecotinamide [the compound of formula (2)] in distilled water was orally 15 administered to the diabetic rats in a dose of 0.1 mg/kg, 0.3 mg/kg, 1.0 mg/kg or 3.0 mg/kg once a day. Distilled water was orally given to rats of a control group once a day.

On the other hand, 3.0 mg/kg of the compound of formula (2) in the form of a solution in distilled water was orally administered to non-diabetic rats, to which streptozotocin had not been injected, once a day. Distilled water was orally given to rats of a control group once a day.

After the administration of the compound of formula (2) or distilled water for two weeks, the rats were anesthetized with thiobutabarbital (trade name: Inactin; 50 to 100 mg/kg i.p.). The carotid artery and trachea were cannulated for blood pressure measurements and artificial respiration, respectively. Sciatic motor nerve conduction velocity in the branch to tibialis anterior muscle, and saphenous sensory nerve conduction velocity were estimated according to a literature (Q. J. Exp. Physiol., 74, 917–926, 1989). For blood flow measurements anaesthetised rats were paralysed with d-tubocurarine and sciatic endoneurial nutritive (capillary) blood flow was measured by microelectrode polarography and hydrogen clearance according to a literature (Am. J. Physiol., 261, E1–E8, 1991). Further, blood samples for estimation of plasma glucose concentration (GOD-Perid method, Boehringer Mannheim GmbH) were taken from the tail vein or carotid cannula at the end of the experiments.

The results are shown in Tables 1 and 2.

Table 1
Effects of Compound of Formula (2) on Body Weights, Plasma Glucose Concentration, Sciatic Motor Nerve Conduction Velocity and Sciatic Motor Endoneurial Blood Flow of Non-Diabetic Rats and Streptozotocin-induced Diabetic Rats

TABLE 1

Effects of compound formula (2) on body weights, plasma glucose concentration, sciatic motor nerve conduction velocity and sciatic motor endoneurial blood flow of non-diabetic rats and streptozotocin-induced diabetic rats

| Test animal | Dose of compound of formula (2) (mg/kg) | Number of rats | Body wt. (g) | Plasma glucose concentration (mM) | Nerve conduction velocity (m/sec) | endo-neutrial blood flow (ml/min/100 g) |
|---|---|---|---|---|---|---|
| Non-diabetic rat | 0.0 | 10 | 447 ± 7 | 6.3 ± 2 | 63.8 ± 0.4 | 18.3 ± 0.8 |
| Non-diabetic rat | 3.0 | 10 | 437 ± 7 | 7.6 ± 0.7 | 63.9 ± 0.5 | 18.2 ± 1.1 |
| Diabetic rat | 0.0 | 10 | 334 ± 8 | 41.2 ± 2 | 51.2 ± 0.5 | 8.4 ± 0.7 |
| Diabetic rat | 0.3 | 14 | 338 ± 11 | 40.8 ± 1.3 | 54.9 ± 0.5 (n = 8) | 10.6 ± 0.8 (n = 8) |
| Diabetic rat | 1.0 | 14 | 345 ± 6 | 41.6 ± 1.2 | 60.7 ± 0.5 (n = 8) | 13.9 ± 0.7 (n = 8) |
| Diabetic rat | 3.0 | 18 | 330 ± 7 | 41.5 ± 1.5 | 63.7 ± 0.4 (n = 14) | 19.1 ± 1.4 (n = 14) |

Table 1 shows the effects of the compound of the present invention on the body weight, plasma glucose concentration, sciatic motor nerve conduction velocity and siatic motor endoneurial blood flow of non-diabetic rats and streptozotocin-induced diabetic rats.

As shown in Table 1, it was confirmed that the body weight of diabetic rats continued to decrease until the completion of the experiments and the plasma glucose concentration was about 6 to 7 times higher than that of the non-diabetic rats. Because the body weight and plasma glucose concentration were unchanged when 0.3 mg/kg to 3.0 mg/kg of the compound of the present invention was orally administered to the non-diabetic rats and diabetic rats, it was confirmed that the compound of the present invention in a dose in the above-described range does not exert any influence on the body weight and the plasma glucose concentration.

It was proved that the compound of the present invention in a dose in the above-described range does not exert any influence on the blood pressure by the fact that when 0.3 to 3.0 mg/kg of the compound was orally administered to the non-diabetic rats and diabetic rats, the blood pressure of them was scarcely changed.

As shown in Table 1, the compound of the present invention significantly increased the sciatic motor nerve conduction velocity and sciatic motor endoneurial blood flow of the diabetic rats, which had been decreased by diabetes, after the administration of the compound for two weeks. FIG. 1 is a graph showing the experimental data of the dose- dependency of sciatic motor endoneurial blood flow shown in Table 1. Particularly in the group in which 3.0 mg/kg of the compound of the present invention was administered to the diabetic rats, the nerve conduction velocity and endoneurial blood flow of the diabetic rats were improved to the ranges of those of the non-diabetic rats. On the other hand, when 3.0 mg/kg of the compound of the present invention was administered to the non-diabetic rats, the nerve conduction velocity and endoneurial blood flow of the rats were unchanged. It is thus apparent from the experimental results that the compound of the present invention has an effect of curing the diabetic neuropathy in rats by improving the endoneurial blood flow and the nerve conduction velocity.

Table 2
Dose Response Effect of the Compound of Formula (2) on the Sciatic Motor Nerve Conduction Velocity and the Saphenous Sensory Nerve Conduction Velocity in Streptozotocin-induced Diabetic Rats.

TABLE 2

Dose response effect of the compound of formula (2) on the sciatic motor nerve conduction velocity and the saphenous sensory nerve conduction velocity in streptozotocin-induced diabetic rats

| Dose of compound of formula (2) (mg/kg) | Sciatic motor nerve conduction velocity (m/sec) | Number of rats | Saphenous sensory nerve conduction velocity (m/sec) | Number of rats |
|---|---|---|---|---|
| 0.1 | 51.5 ± 0.7 | 7 | 54.0 ± 0.7 | 7 |
| 0.3 | 54.9 ± 0.5 | 8 | 58.8 ± 0.8 | 8 |
| 1.0 | 60.7 ± 0.5 | 8 | 60.2 ± 0.6 | 8 |
| 3.0 | 63.7 ± 0.4 | 14 | 60.7 ± 0.6 | 8 |

Figure 2A:
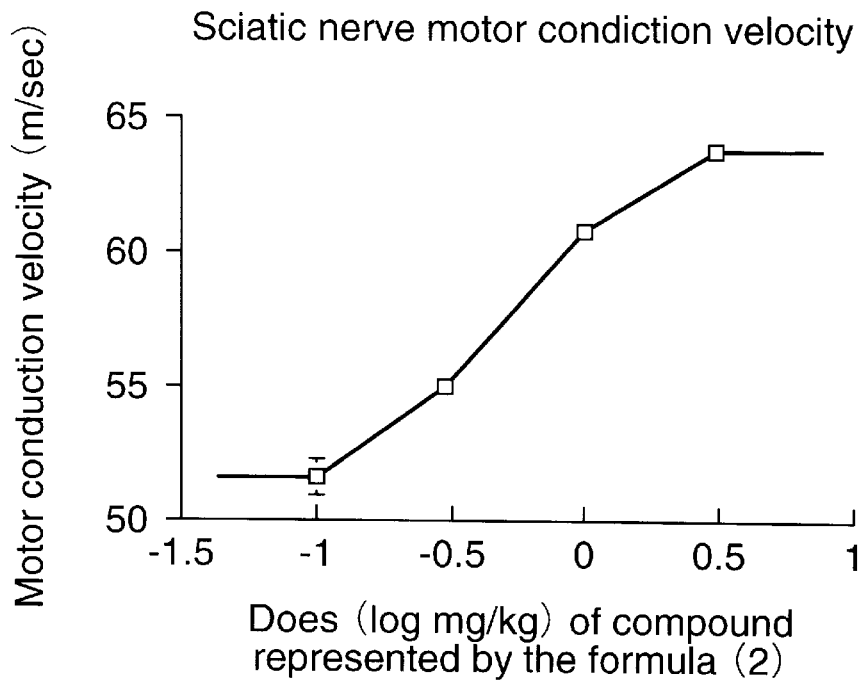
FIG. 2 shows the dose response effect of the compound of formula (2) on the sciatic motor nerve conduction velocity and the saphenous sensory nerve conduction velocity in diabetic rats.
Figure 2B:
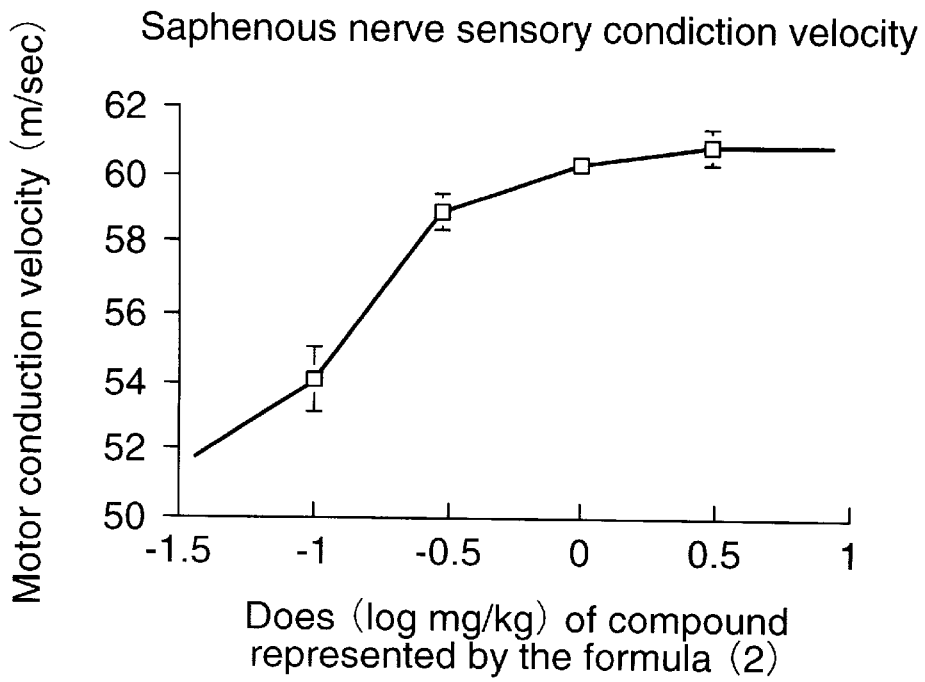

Table 2 shows the dose response effect of the compound of formula (2) on the sciatic motor nerve conduction velocity and the saphenous sensory nerve conduction velocity of streptozotocin-induced diabetic rats on the dose of the compound of the present invention. FIG. 2 is a graph showing the experimental data of the dose response effect of the compound of formula (2) on the sciatic motor nerve conduction velocity and the saphenous sensory nerve conduction velocity on the dose as shown in Table 2. As shown in Table 2 and FIG. 2, the compound of the present invention dose-dependently increased the sciatic motor nerve conduction velocity and saphenous sensory nerve conduction velocity of the diabetic rats, which had been lowered by diabetes, after the administration of the compound for two weeks. Particularly in the group in which 3.0 mg/kg of the compound of the present invention was administered to the diabetic rats, the sciatic motor nerve conduction velocity and saphenous sensory nerve conduction velocity were improved to the levels of those of the non-diabetic rats. The sciatic motor nerve conduction velocity was significantly improved with at least 0.3 mg/kg of the compound, and the saphenous sensory nerve conduction velocity was significantly improved with at least 0.1 mg/kg of the compound. It is thus apparent from the experimental results that the compounds of the present invention are capable of dose-independently improving both motor nerve conduction velocity and the sensory nerve conduction velocity and also that particularly, the saphenous sensory nerve conduction velocity was significantly improved with the compound in a dose smaller than that used for improving the sciatic motor nerve conduction velocity.

When the pharmaceutical composition of the present invention containing the piperidine derivative or the pharmaceutically acceptable salt thereof as the effective ingredient is used in a dose which does not lower the blood pressure, the endoneurial blood flow is dose-independently improved, and both sciatic motor nerve conduction velocity and saphenous sensory nerve conduction velocity were dose-dependently improved. It is thus expected that the pharmaceutical composition is effective for the treatment and prevention of diabetic neuropathy.

What is claimed is:

1. A method for treating diabetic neuropathy comprising:

administering to a patient suffering from diabetic neuropathy an effective amount of the piperidine compound of formula (1):

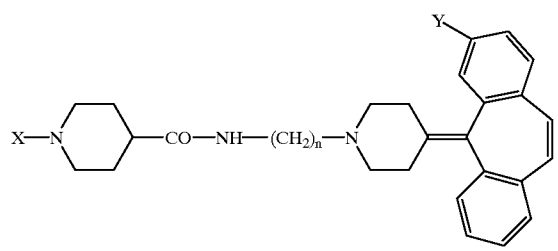

(1)

wherein n is an integer of 2 or 3,

Y is a hydrogen atom or a halogen atom, and

X is a formyl group, acetyl group or a hydrogen atom.

2. The method of claim 1, wherein n is 2, Y is hydrogen and X is a formyl group.

3. The method of claim 2, wherein the piperidine compound is orally administered.

4. The method of claim 1, wherein said piperidine compound is administered at a dosage that increases endoneutrial blood flow.

* * * * *